US009469658B2

(12) United States Patent
Qin et al.

(10) Patent No.: US 9,469,658 B2
(45) Date of Patent: Oct. 18, 2016

(54) LANTHANIDE COMPLEX CATALYST AND POLYMERIZATION METHOD EMPLOYING SAME

(75) Inventors: Zengquan Qin, Copley, OH (US); Steven Luo, Copley, OH (US); Joshua S. Dickstein, Copley, OH (US)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 13/983,718

(22) PCT Filed: Feb. 5, 2012

(86) PCT No.: PCT/US2012/023909
§ 371 (c)(1),
(2), (4) Date: Oct. 15, 2013

(87) PCT Pub. No.: WO2012/106697
PCT Pub. Date: Aug. 9, 2012

(65) Prior Publication Data
US 2014/0039126 A1    Feb. 6, 2014

Related U.S. Application Data

(60) Provisional application No. 61/439,862, filed on Feb. 5, 2011.

(51) Int. Cl.
*C08F 4/54*        (2006.01)
*C07F 5/00*        (2006.01)
*C08F 36/06*       (2006.01)
*C08F 4/52*        (2006.01)
*C08F 136/06*      (2006.01)
*C08F 236/06*      (2006.01)

(52) U.S. Cl.
CPC ............. *C07F 5/003* (2013.01); *C08F 4/52* (2013.01); *C08F 4/545* (2013.01); *C08F 36/06* (2013.01); *C08F 136/06* (2013.01); *C08F 236/06* (2013.01)

(58) Field of Classification Search
CPC .......... C08F 4/54; C08F 5/545; C08F 36/00; C08F 136/06; C08F 236/06
USPC .............................................. 556/1; 502/102
IPC ......................................................... C08F 4/44
See application file for complete search history.

(56) References Cited

U.S. PATENT DOCUMENTS

| | | | | |
|---|---|---|---|---|
| 6,309,997 B1 * | 10/2001 | Fujita et al. | .................. | 502/167 |
| 6,569,799 B1 | 5/2003 | Barbotin et al. | | |
| 6,770,723 B2 | 8/2004 | Fujita et al. | | |
| 6,800,705 B2 | 10/2004 | Barbotin et al. | | |
| 7,094,854 B2 | 8/2006 | Monteil et al. | | |
| 7,300,903 B2 | 11/2007 | Fujita et al. | | |
| 7,547,654 B2 | 6/2009 | Boisson et al. | | |
| 2009/0281260 A1 * | 11/2009 | Makio et al. | .................. | 526/172 |
| 2010/0273763 A1 * | 10/2010 | Brard | .................. | C07F 13/005 |
| | | | | 514/186 |
| 2012/0029167 A1 * | 2/2012 | Ishikawa | .............. | A61K 31/135 |
| | | | | 530/323 |
| 2012/0123070 A1 | 5/2012 | Boisson et al. | | |
| 2014/0031503 A1 | 1/2014 | Qin et al. | | |
| 2015/0259361 A1 | 9/2015 | Luo et al. | | |

FOREIGN PATENT DOCUMENTS

| | | | | |
|---|---|---|---|---|
| JP | 2010-174160 A * | 8/2010 | ............. | C08G 65/10 |
| WO | 2004/044018 A2 | 5/2004 | | |
| WO | WO 2010/058280 A1 * | 5/2010 | ........... | C07C 251/24 |
| WO | 2012/106694 A2 | 8/2012 | | |

OTHER PUBLICATIONS

Dubé, T.; Gambarotta, S.; Yap, G. Organometallics 1998, 17, 3967-3973.*
Liu et al., Dalton Trans., 2008, 6170-6178.*
Yang et al. Chem. Commun., 2008, 3266-3268.*
Dubé et al. Organometallics, 1998, 17, 3967-3973.*
Ganjali et al. Analytical Sciences, 2002, 18, 289-292.*
Ni et al. Chinese J. Catal. 2010, 31(8), 965-971.*
Tripathi et al. Synth. React. Inorg. Metal-Org. Chem. 2000, 30, 139-155.*
Broderick et al. Chem. Commun. 2011, 47, 9897-9899.*
Yadawe et al. Research Journal of Chemistry and Environment 2011, 15, 27-31.*
Zhou et al. Guangpuxue Yu Guangpu Fenxi (Spectroscopy and Spectral Analysis) 2010, 30(5), 1386-1390.*
C. Cappacchione et al., "Ethylene-butadiene copolymerization promoted by Titamium Complex containing a Tetradentate [OSSO]-Type Bis(phenolato) Ligand," Macromolecules, 2008, 41, pp. 4573-4575 (courtesy copy).
C. Cappacchione et al., "Copolymerization of Ethylene with Isoprene Promoted by Titanium Complexes Containing a Tetradentate [OSSO]-Type Bis(phenolato) Ligand," J. Poly. Sci.: Part A: Polymer Chemistry, vol. 48, pp. 4200-4206 (2010, Wiley Periodicals, Inc.).
J. Thuilliez et al., "Alternating Copolymerization of Ethylene and Butadiene with a Neodymocene Catalyst," Angew. Chem. Int. Ed., 2005, 44, 2593-96 (2005, Wiley-VCH Verlag GmbH & Co,; Wernheim, Germany).
T.J. Woodman et al., "Heterogenized 'Ligand-Free' Lanthanide Catalysts for the Homo- and Copolymerization of Ethylene and 1,3-Butadiene," Macromolecules, 2005, 38, pp. 3060-3067 (2005, American Chemical Society; Washington, DC).
P.G. Cozzi, "Metal-Salen Schiff base complexes in catalysis: practical aspects," Chem. Soc. Rev., 2004, 33, pp. 410-421 (2004, The Royal Society of Chemistry; London, England).
N. Xufeng et al., "Controlled Ring-Opening Polymerization of E-Captolactone Catalyzed by a Rare Earth Schiff-Base Complex," Chin. J. Catal., 2010, 31, pp. 965-971 (2010, Elsevier BV; Amsterdam, NL).

(Continued)

*Primary Examiner* — Rip A Lee
(74) *Attorney, Agent, or Firm* — Meredith E. Hooker; David G. Burleson

(57) ABSTRACT

A novel class of lanthanide metal salen complexes can be used as an ingredient of a catalyst system. The catalyst system can be used in polymerizations of ethylenically unsaturated hydrocarbon monomers.

18 Claims, No Drawings

(56) References Cited

OTHER PUBLICATIONS

J. Wu et al., "Synthesis, Structural Characterization and Olefin Polymerization Behavior of Vanadium(III) Complexes Bearing Tridentate Schiff Base Ligands," Organometallics, 2009, vol. 28, No. 6, pp. 1817-1825 (2009, American Chemical Society; Washington, DC).

Extended search report prepared by EPO in EP 12742527.0, mailed Jul. 9, 2014-6 pp.

Official action mailed by EPO on Apr. 1, 2015, in EP appl. No. 12 742 527.0—4 pp.

Official action mailed by SIPO on Nov. 19, 2014, in CN appl. No. 201280016031.5—7 pp. + 8-pg translation.

Q. Liu et al., "Cationic rare-earth metal SALEN complexes," Dalton Trans., 2008, pp. 6170-6178 (The Royal Society of Chemistry; London, England).

Official action mailed by SIPO on Aug. 6, 2015, in CN appl. No. 201280016031.5—3 pp. +5-pg translation.

W. Miao et al., "Rare earth metal alkyl complexes bearing N,O,P multidentate ligands: Synthesis, characterization and catalysis on the ring-opening polymerization of L-lactide," J. Organometallic Chem., 692 (2007), pp. 3823-34 (Elsevier B.V.; Amsterdam, Netherlands).

* cited by examiner

LANTHANIDE COMPLEX CATALYST AND POLYMERIZATION METHOD EMPLOYING SAME

CROSS-REFERENCE TO RELATED APPLICATION

This is a national stage entry application of international application no. PCT/US2012/023909, filed 5 Feb. 2012, and claims the benefit of U.S. provisional patent application No. 61/439,862, filed 5 Feb. 2011, the disclosure of which is incorporated herein by reference.

BACKGROUND INFORMATION

Rubber goods such as tire treads often are made from elastomeric compositions that contain one or more reinforcing materials such as, for example, particulate carbon black and silica; see, e.g., *The Vanderbilt Rubber Handbook,* 13th ed. (1990), pp. 603-04.

Good traction and resistance to abrasion are primary considerations for tire treads; however, motor vehicle fuel efficiency concerns argue for a minimization in their rolling resistance, which correlates with a reduction in hysteresis and heat build-up during operation of the tire. (A reduction in hysteresis commonly is determined by a decrease in tan δ value at an elevated temperature, e.g., 50° or 60° C. Conversely, good wet traction performance commonly is considered to be associated with an increase in tan δ value at a low temperature, e.g., 0° C.)

Reduced hysteresis and traction are, to a great extent, competing considerations: treads made from compositions designed to provide good road traction usually exhibit increased rolling resistance and vice versa.

Filler(s), polymer(s), and additives typically are chosen so as to provide an acceptable compromise or balance of these properties. Ensuring that reinforcing filler(s) are well dispersed throughout the elastomeric material(s) both enhances processability and acts to improve physical properties. Dispersion of fillers can be improved by increasing their interaction with the elastomer(s), which commonly results in reductions in hysteresis (see above). Examples of efforts of this type include high temperature mixing in the presence of selectively reactive promoters, surface oxidation of compounding materials, surface grafting, and chemically modifying the polymer, typically at a terminus thereof.

Various elastomeric materials often are used in the manufacture of vulcanizates such as, e.g., tire components. In addition to natural rubber, some of the most commonly employed include high-cis polybutadiene, often made by processes employing catalysts, and substantially random styrene/butadiene interpolymers, often made by processes employing anionic initiators. Functionalities that can be incorporated into catalyzed polymers often cannot be incorporated into anionically initiated polymers and vice versa.

Of particular difficulty to synthesize are interpolymers of olefins and polyenes, particularly conjugated dienes, due in large part to their very different reactivities, i.e., susceptibility to coordinate with catalytic metal atoms and thereby polymerize. Although difficult to synthesize, such interpolymers have many commercial uses.

SUMMARY

Any of a class of lanthanide metal complexes can be used as an ingredient of a catalyst system. The catalyst system can be used in polymerizations of ethylenically unsaturated hydrocarbon monomers.

The class of lanthanide metal complexes can be represented by the general formula

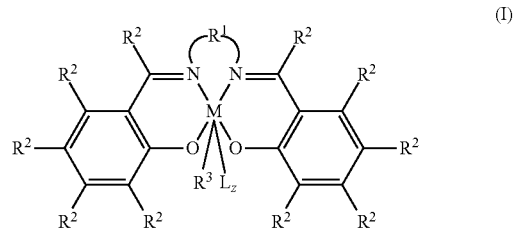

where M represents a lanthanide metal atom; L represents a neutral Lewis base; z is an integer of from 0 to 2 inclusive; $R^1$ is a divalent atom or group that contains at least one of C, O, S, N, P, Si, Se, Sn or B; each $R^2$ independently is H, a halogen atom, substituted or unsubstituted hydrocarbyl group, the radical of a heterocyclic compound, or a heteroatom-containing group; and $R^3$ is a halogen-containing group, a group that contains an Al atom, or $R^2$. In the foregoing, two $R^2$ groups or one $R^2$ group and $R^1$ or $R^3$, together with the atoms to which each is bonded, can form a ring structure. Alternatively or additionally, $R^1$ and $R^3$, together with the atoms to which each is bonded, can form a ring structure. Methods of making this complex also are provided.

In other aspects are provided a catalyst composition that includes the lanthanide metal complex set forth above with a catalyst activator, as well as methods of making the composition.

In a still further aspect is provided a process of polymerizing ethylenically unsaturated hydrocarbon monomers. The method involves contacting the monomers with the aforedescribed catalyst composition. The ethylenically unsaturated hydrocarbon monomers can include one or more types of polyene and, optionally, one or more types of olefin. Where one or more types of olefin are present in the monomers, the resulting interpolymer typically contains at least 50 mole percent polyene mer.

The foregoing process also can include providing the resulting polymer with a terminal moiety so as to enhance the ability of the polymer to interact with particulate filler such as, e.g., carbon black and/or silica. Compositions, including vulcanizates, that include particulate fillers and such polymers also are provided, as are methods of providing and using such compositions.

Other aspects of the invention will be apparent to the ordinarily skilled artisan from the detailed description that follows. To assist in understanding that description, certain definitions are provided immediately below, and these are intended to apply throughout unless the surrounding text explicitly indicates a contrary intention:

"polymer" means the polymerization product of one or more monomers and is inclusive of homo-, co-, ter-, tetra-polymers, etc.;

"mer" or "mer unit" means that portion of a polymer derived from a single reactant molecule (e.g., ethylene mer has the general formula —$CH_2CH_2$—);

"copolymer" means a polymer that includes mer units derived from two reactants, typically monomers, and is inclusive of random, block, segmented, graft, etc., copolymers;

"interpolymer" means a polymer that includes mer units derived from at least two reactants, typically monomers, and is inclusive of copolymers, terpolymers, tetra-polymers, and the like;

"substituted" means containing a heteroatom or functionality (e.g., hydrocarbyl group) that does not interfere with the intended purpose of the group in question;

"heteroatom," when used in the phrase "heteroatom-containing group," means O, S, N, B, P, Si, Ge or Sn;

"heterocyclic compound" means a cyclic compound that includes within the ring structure a heteroatom;

"polyene" means a molecule, typically a monomer, with at least two double bonds located in the longest portion or chain thereof, and specifically is inclusive of dienes, trienes, and the like;

"polydiene" means a polymer that includes mer units from one or more dienes;

"phr" means parts by weight (pbw) per 100 pbw rubber;

"radical" means the portion of a molecule that remains after reacting with another molecule, regardless of whether any atoms are gained or lost as a result of the reaction;

"non-coordinating anion" means a sterically bulky anion that does not form coordinate bonds with, for example, the active center of a catalyst system due to steric hindrance;

"non-coordinating anion precursor" means a compound that is able to form a non-coordinating anion under reaction conditions;

"ring system" means a single ring or two or more fused rings or rings linked by a single bond, with the proviso that each ring includes unsaturation;

"terminus" means an end of a polymeric chain;

"terminally active" means a polymer with a living or pseudo-living terminus; and "terminal moiety" means a group or functionality located at a terminus.

Throughout this document, all values given in the form of percentages are weight percentages unless the surrounding text explicitly indicates a contrary intention. The relevant portion(s) of any specifically referenced patent and/or published patent application are incorporated herein by reference.

DETAILED DESCRIPTION OF ILLUSTRATIVE EMBODIMENTS

As apparent from the foregoing, the catalyst composition can be used to polymerize polyenes and, optionally, olefins. The resulting polymer can be elastomeric, including mer units that include ethylenic unsaturation. Mer units that include ethylenic unsaturation can be derived from polyenes, particularly dienes and trienes (e.g., myrcene). Illustrative polyenes include $C_4$-$C_{30}$ dienes, preferably $C_4$-$C_{12}$ dienes. Preferred among these are conjugated dienes such as, but not limited to, 1,3-butadiene, 1,3-pentadiene, 1,3-hexadiene, 1,3-octadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, and the like.

Polyenes can incorporate into polymeric chains in more than one way, and controlling this manner of incorporation can be desirable, particularly for tire tread applications. A polymer chain with an overall 1,2-microstructure, given as a numerical percentage based on total polyene content, of from ~10 to ~80%, optionally from ~25 to ~65%, can be desirable for certain end use applications. A polymer that has an overall 1,2-microstructure of no more than ~50%, preferably no more than ~45%, more preferably no more than ~40%, even more preferably no more than ~35%, and most preferably no more than ~30%, based on total polyene content, is "substantially linear." For certain end use applications, however, keeping the content of 1,2-linkages even lower—e.g., to less than 20%, less than 15%, less than 10%, less than 7%, less than 5%, less than 2%, or less than 1%—can be desirable.

For those polyene mer not having 1,2-microstructure, i.e., those having a 1,4-linkage, such mer can incorporate in either a cis or trans configuration. The present process can provide polymers with polydiene mer having a cis-1,4-linkage content of at least ~60%, at least ~75%, at least ~85%, at least ~90%, and even at least ~95%.

Examples of olefins that can be employed in the process include $C_2$-$C_{30}$ straight chain or branched α-olefins such as ethylene, propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene, 1-eicosene, and the like, as well as $C_3$-$C_{30}$ cycloolefins such as cyclopentene, cycloheptene, norbornene, 5-methyl-2-norbornene, and tetracyclododecene. Smaller olefins such as ethylene and propylene are preferred.

The polymerization process can provide an olefin/polyene interpolymer with a predominant amount of polyene mer, e.g., an olefin/conjugated diene copolymer that includes a predominant amount of conjugated diene mer. The resulting interpolymer can contain up to 10, 20 or even 30 mole percent olefin mer and at least 70, 80 or even 90 mole percent polyene mer. The interpolymer can include from 1 to 30 mole percent olefin mer and from 70 to 99 mole percent conjugated diene mer, from 1 to 20 mole percent olefin mer and from 80 to 99 mole percent conjugated diene mer, or from 1 to 10 mole percent olefin mer and from 10 to 99 mole percent conjugated diene mer.

The number average molecular weight ($M_n$) of the polymer typically is such that a quenched sample exhibits a gum Mooney viscosity ($ML_4$/100° C.) of from ~2 to ~150, more commonly from ~2.5 to ~125, even more commonly from ~5 to ~100, and most commonly from ~10 to ~75; the foregoing generally corresponds to a molecular weight of from ~5,000 to ~250,000 Daltons, commonly from ~10,000 to ~150,000 Daltons, more commonly from ~50,000 to ~120,000 Daltons, and most commonly from ~10,000 to ~100,000 Daltons or even 10,000 to 80,000 Daltons. The resulting interpolymer typically has a molecular weight distribution ($M_w/M_n$) of from 1 to 5, commonly from 2 to 5, more commonly from ~2.0 to ~4.0. (Both $M_n$ and $M_w$ can be determined by GPC calibrated with polystyrene standards.)

The foregoing types of polymers can be made by solution polymerization, which affords exceptional control of properties as randomness, microstructure, etc. Solution polymerizations have been performed since about the mid-20th century, so the general aspects thereof are known to the ordinarily skilled artisan; nevertheless, certain aspects are provided here for convenience of reference.

Suitable solvents include those organic compounds that do not undergo polymerization or incorporation into propagating polymer chains (i.e., are inert toward and unaffected by the catalyst composition) and preferably are liquid at ambient temperature and pressure. Examples of suitable organic solvents include hydrocarbons with a low or relatively low boiling point such as aromatic hydrocarbons, aliphatic hydrocarbons, and cycloaliphatic hydrocarbons. Exemplary polymerization solvents include various $C_5$-$C_{12}$ cyclic and acyclic alkanes (e.g., n-pentane, n-hexane, n-heptane, n-octane, n-nonane, n-decane, isopentane, isohexanes, isopentanes, isooctanes, 2,2-dimethylbutane, cyclopentane, cyclohexane, methylcyclopentane, methylcyclohexane, etc.) as well as their alkylated derivatives, certain liquid aromatic compounds (e.g., benzene, toluene, xylenes, ethylbenzene, diethylbenzene, and mesitylene), petroleum ether, kerosene, petroleum spirits, and mixtures thereof. Other potentially suitable organic compounds that can be used as solvents include high-boiling hydrocarbons of high molecular weights such as paraffinic oil, aromatic oil, or other hydrocarbon oils that are commonly used to oil-extend polymers. The ordinarily skilled artisan is aware of other useful solvent options and combinations.

In solution polymerizations, vinyl content (i.e., 1,2-microstructure) can be adjusted through inclusion of a coordinator, usually a polar compound, in the polymerization ingredients. Up to 90 or more equivalents of coordinator can be used per equivalent of initiator, with the amount depending on, e.g., the amount of vinyl content desired, the level of non-polyene monomer employed, the reaction temperature, and nature of the specific coordinator employed. Compounds useful as coordinators include organic compounds that include a heteroatom having a non-bonded pair of electrons (e.g., O or N). Examples include dialkyl ethers of mono- and oligo-alkylene glycols; crown ethers; tertiary amines such as tetramethylethylene diamine; THF; THF oligomers; linear and cyclic oligomeric oxolanyl alkanes (see, e.g., U.S. Pat. No. 4,429,091) such as 2,2-bis(2'-tetrahydrofuryl)propane, dipiperidyl ethane, hexamethylphosphoramide, N,N'-dimethylpiperazine, diazabicyclooctane, diethyl ether, tributylamine, and the like.

Although the ordinarily skilled artisan understands the conditions typically employed in solution polymerization, a representative description is provided for convenience of the reader. The following is based on a batch process, although extending this description to, e.g., semi-batch or continuous processes is within the capability of the ordinarily skilled artisan.

Certain end use applications call for polymers that have properties that can be difficult or inefficient to achieve via anionic (living) polymerizations. For example, in some applications, conjugated diene polymers having high cis-1,4-linkage contents can be desirable, and these commonly are prepared by processes using catalysts (as opposed to the initiators employed in living polymerizations) and may display pseudo-living characteristics.

The polymerization process employs a lanthanide catalyst composition. The term "catalyst composition" encompasses a simple mixture of ingredients, a complex of various ingredients that is caused by physical or chemical forces of attraction, a chemical reaction product of some or all of the ingredients, or a combination of the foregoing.

Commonly employed lanthanide catalyst compositions include (a) a lanthanide compound, an alkylating agent and optionally a halogen-containing compound (where neither the lanthanide compound or the alkylating agent contains a halogen atom); (b) a lanthanide compound and an aluminoxane; or (c) a lanthanide compound, an alkylating agent, and a non-coordinating anion or precursor thereof.

The polymerization process described herein employs a specific group of lanthanide complexes, specifically, those defined by formula (I) set forth above. The following paragraphs refer to that group of complexes.

In formula (I), M represents a lanthanide metal atom, i.e., elements with atomic numbers 57 to 71: La, Ce, Pr, Nd, Pm, Sm, Eu, Gd, Tb, Dy, Ho, Er, Tm, Yb, and Lu. Preferred lanthanide metals are Nd and Gd. M can be in any of a number of oxidation states, with +2 to +5 being most common and +3 being perhaps the most common.

L represents a neutral Lewis base, examples of which include but not limited to (thio)ethers, cyclic (thio)ethers, amines, cyclic amines, phosphines, and cyclic phosphines. Specific non-limiting examples of L groups include THF, diethyl ether, dimethyl aniline, trimethyl phosphine, neutral olefins, neutral diolefins, and the like.

Because z can be an integer of from 0 to 2 (determined by the available coordination number(s) of M), the complex can contain a plurality of L groups. In the case where z is 2, each L can be the same or different.

$R^1$ is a divalent group that contains at least one of C, O, S, N, P, Si, Se, Sn or B. Those of the foregoing elements which are (or can be) divalent, e.g., O, S and Se, can act as a divalent "group," while the other elements can constitute part of a multi-atom group, preferably one with 2-40, more preferably with 2-10, atoms in the longest chain thereof. Specific non-limiting examples of multi-atom $R^1$ divalent groups include NH, PH, BH, BF, $SiH_2$, $SnH_2$ and NR, PR, BR, $SiR_2$ or $SnR_2$ where R is a hydrocarbyl group, preferably a $C_1$-$C_3$ alkyl group.

Each $R^2$ independently is H, a halogen atom (i.e., F, Cl, Br or I), a substituted or unsubstituted hydrocarbyl group, the radical of a heterocyclic compound, or a heteroatom-containing group; if an $R^2$ is a halogen, it preferably is Cl or Br. In some embodiments, two or more $R^2$ groups together with the C atoms to which each is bonded can form a ring structure. In other embodiments, one or more $R^2$ groups and $R^1$, together with the atoms to which each is bonded, can form a ring structure. The resulting ring structure(s) can be aliphatic, aromatic or heterocyclic and optionally can contain one or more substituents.

$R^3$ is a halogen-containing group such as $PF_5$, $BF_3$, $ClO_4$, $SbCl_6$, $IO_4$, and the like; a group that contains an Al atom; or $R^2$. If an $R^3$ is a halogen, it preferably is Cl or Br, with Cl being particularly preferred as $R^3$. Alternatively, $R^3$ with an $R^2$ group (or less frequently an $R^1$ group), together with the atoms to which each is bonded, can form a ring.

Exemplary hydrocarbyl groups include straight-chain or branched $C_1$-$C_{30}$ alkyl groups such as methyl, ethyl, n-propyl, isopropyl, n-butyl, isobutyl, sec-butyl, tert-butyl, neopentyl, n-hexyl, octyl and the like; straight-chain or branched $C_2$-$C_{30}$ alkenyl groups such as vinyl, allyl, and isopropenyl; straight-chain or branched $C_2$-$C_{30}$ alkynyl groups such as ethynyl and propargyl; $C_2$-$C_{30}$ saturated cyclic groups such as cyclopropyl, cyclobutyl, cyclopentyl, cyclohexyl, and adamantyl; $C_5$-$C_{30}$ unsaturated cyclic groups such as cyclopentadienyl, indenyl, and fluorenyl; and $C_6$-$C_{30}$ aryl groups such as phenyl, tolyl, benzyl, naphthyl, biphenyl, phenanthryl, antracenyl and terphenyl.

The hydrocarbyl groups can be substituted with halogen atoms (e.g., halogenated $C_1$-$C_{30}$ hydrocarbyl groups such as trifluoromethyl, pentafluorophenyl, and chlorophenyl), other hydrocarbyl groups (e.g., aryl-substituted alkyl groups such as benzyl and cumyl), heteroatom-containing groups (e.g., alkoxy, aryloxy such as 2,6-dimethylphenoxy or 2,4,6-trimethylphenoxy, acyl such as p-chlorobenzoyl or p-methoxybenzoyl, (thio)carboxyl, carbonato, hydroxy, peroxy, (thio)ester such as acetyloxy or benzoyloxy, (thio)ether, anhydride, amino, imino, amide such as acetamido or N-methylacetamido, imide such as acetimido and benzimido, hydrazino, hydrazono, nitro, nitroso, cyano, isocyano, (thio)cyanic acid ester, amidino, diazo, borandiyl, borantriyl, diboranyl, mercapto, dithioester, alkylthio, arylthio such as (methyl)phenylthio, or naphthylthio, thioacyl, isothiocyanic acid ester, sulfonester, sulfonamide, dithiocarboxyl, sulfo, sulfonyl, sulfinyl, sulfenyl, phosphido, (thio)-phosphoryl, phosphato, silyl, siloxy, hydrocarbyl-substituted silyl groups such as methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl, dimethyl(pentafluorophenyl)silyl, bistrimethylsilylmethyl, and hydrocarbyl-substituted siloxy groups such as trimethylsiloxy), and the like. (Replacing the silicon atom in the Si-containing groups with Ge or Sn can provide useful Ge- or Sn-containing groups.) The Al- and B-containing groups can be represented, respectively, by $AlR^5_4$ and $BR^5_m$ where m is 2 or 3 and $R^5$ is H, a halogen atom, a substituted or unsubstituted aryl group, etc.

Preferred hydrocarbyl groups include straight-chain or branched $C_1$-$C_{30}$ alkyl groups, $C_6$-$C_{30}$ aryl groups, and aryl groups substituted with 1 to 5 substituents, such as $C_1$-$C_{30}$ alkyl or alkoxy groups and $C_6$-$C_{30}$ aryl or aryloxy groups.

Exemplary heterocyclic compounds include N-containing heterocycles such as pyrrole, pyridine, pyrimidine, quinoline, and triazine, O-containing heterocycles such as furan and pyran, and S-containing heterocycles such as thiophene. The heterocyclic compounds can include substituents such as, but not limited to, $C_1$-$C_{20}$ alkyl or alkoxy groups.

Formula I-type compounds can be prepared following the procedures described in, for example, U.S. Pat. No. 7,300,903 (and substituting a lanthanide series metal compound for the transition metal compounds used there). The examples section below contains specific exemplary procedures.

Component (b) of the lanthanide catalyst composition, referred to herein as a co-catalyst or catalyst activator, includes an alkylating agent and/or a compound containing a non-coordinating anion or a non-coordinating anion precursor.

An alkylating agent can be considered to be an organometallic compound that can transfer hydrocarbyl groups to another metal. Typically, these agents are organometallic compounds of electropositive metals such as Groups 1, 2, and 3 metals. Exemplary alkylating agents include organoaluminum compounds such as those having the general formula $AlR^6_nX_{3-n}$ (where n is an integer of from 1 to 3 inclusive; each $R^6$ independently is a monovalent organic group, which may contain heteroatoms such as N, O, B, Si, S, P, and the like, connected to the Al atom via a C atom; and each X independently is H, a halogen atom, a carboxylate group, an alkoxide group, or an aryloxide group). In one or more embodiments, each $R^6$ independently can be a hydrocarbyl group such as, for example, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group containing from 1 C atom, or the appropriate minimum number of C atoms to form the group, up to ~20 C atoms. These hydrocarbyl groups may contain heteroatoms including, but not limited to, N, O, B, Si, S, and P atoms. Non-limiting species of organoaluminum compounds within this general formula include trihydrocarbylaluminum compounds such as trimethylaluminum, triethylaluminum, triisobutylaluminum, tri-n-propylaluminum, triisopropylaluminum, tri-n-butylaluminum, tri-t-butylaluminum, tri-n-pentylaluminum, trineopentylaluminum, tri-n-hexylaluminum, tri-n-octylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, and ethyldi-benzylaluminum;

dihydrocarbylaluminum hydrides such as diethylaluminum hydride, di-n-propylaluminum hydride, diisopropylaluminum hydride, di-n-butylaluminum hydride, diisobutylaluminum hydride, di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-nbutylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride;

hydrocarbylaluminum dihydrides such as ethylaluminum dihydride, n-propylaluminum dihydride, isopropylaluminum dihydride, nbutylaluminum dihydride, isobutylaluminum dihydride, and n-octylaluminum dihydride;

dihydrocarbylaluminum carboxylates;

hydrocarbylaluminum bis(carboxylate)s;

dihydrocarbylaluminum alkoxides;

hydrocarbylaluminum dialkoxides;

dihydrocarbylaluminum halides such as diethylaluminum chloride, di-n-propylaluminum chloride, diisopropylaluminum chloride, di-n-butylaluminum chloride, diisobutylaluminum chloride, di-n-octylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenyl-n-butylaluminum chloride, phenylisobutylaluminum chloride, phenyl-n-octylaluminum chloride, ptolylethylaluminum chloride, p-tolyl-n-propylaluminum chloride, p-tolylisopropylaluminum chloride, p-tolyl-n-butylaluminum chloride, p-tolylisobutylaluminum chloride, p-tolyl-noctylaluminum chloride, benzylethylaluminum chloride, benzyl-n-propylaluminum chloride, benzylisopropylaluminum chloride, benzyl-n-butylaluminum chloride, benzylisobutylaluminum chloride, and benzyl-n-octylaluminum chloride;

hydrocarbylaluminum dihalides such as ethylaluminum dichloride, n-propylaluminum dichloride, isopropylaluminum dichloride, n-butylaluminum dichloride, isobutylaluminum dichloride, and n-octylaluminum dichloride;

dihydrocarbylaluminum aryloxides; and hydrocarbylaluminum diaryloxides.

In certain embodiments, the alkylating agent can include trihydrocarbylaluminum, dihydrocarbylaluminum hydride, and/or hydrocarbylaluminum dihydride.

Other organoaluminum compounds that can serve as alkylating agents include, but are not limited to, dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, and isobutylaluminum diphenoxide.

Another class of organoaluminum compounds suitable for use as an alkylating agent is aluminoxanes. This class includes oligomeric linear aluminoxanes and oligomeric cyclic aluminoxanes, formulas for both being provided in a variety of references including, for example, U.S. Pat. No. 8,017,695. (Where the oligomeric type of compound is used as an alkylating agent, the number of moles refers to the number of moles of Al atoms rather than the number of moles of oligomeric molecules, a convention commonly employed in the art of catalyst systems utilizing aluminoxanes.)

Aluminoxanes can be prepared by reacting trihydrocarbylaluminum compounds with water. This reaction can be performed according to known methods such as, for example, (1) dissolving the trihydrocarbylaluminum compound in an organic solvent and then contacting it with water, (2) reacting the trihydrocarbylaluminum compound with water of crystallization contained in, for example, metal salts, or water adsorbed in inorganic or organic compounds, or (3) reacting the trihydrocarbylaluminum compound with water in the presence of the monomer(s) to be polymerized.

Suitable aluminoxane compounds include, but are not limited to, methylaluminoxane ("MAO"), modified methylaluminoxane ("MMAO," formed by substituting ~20 to 80% of the methyl groups of MAO with $C_2$-$C_{12}$ hydrocarbyl groups, preferably with isobutyl groups, using known techniques), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cyclohexylaluminoxane, 1-methylcyclopentylaluminoxane, phenylaluminoxane, and 2,6-dimethylphenylaluminoxane.

Aluminoxanes can be used alone or in combination with other organoaluminum compounds. In one embodiment, MAO and at least one other organoaluminum compound such as diisobutyl aluminum hydride can be employed in combination. The interested reader is directed to U.S. Patent Publ. No. 2008/0182954 for other examples of aluminoxanes and organoaluminum compounds employed in combination.

Also suitable as alkylating agents are organomagnesium compounds such as those having the general formula $R^7_m MgX_{2-m}$ where X is defined as above, m is 1 or 2, and $R^7$ is the same as $R^6$ except that each monovalent organic group is connected to the Mg atom via a C atom. Potentially useful organomagnesium compounds include, but are not limited to, diethylmagnesium, di-n-propylmagnesium, diisopropylmagnesium, dibutylmagnesium, dihexylmagnesium, diphenylmagnesium, dibenzylmagnesium, hydrocarbylmagnesium hydride (e.g., methylmagnesium hydride, ethylmagnesium hydride, butylmagnesium hydride, hexylmagnesium hydride, phenylmagnesium hydride, benzylmagnesium hydride), hydrocarbylmagnesium halide (e.g., methylmagnesium chloride, ethylmagnesium chloride, butylmagnesium chloride, hexylmagnesium chloride, phenylmagnesium chloride, benzylmagnesium chloride, methylmagnesium bromide, ethylmagnesium bromide, butylmagnesium bromide, hexylmagnesium bromide, phenylmagnesium bromide, benzylmagnesium bromide), hydrocarbylmagnesium carboxylate (e.g., methylmagnesium hexanoate, ethylmagnesium hexanoate, butylmagnesium hexanoate, hexylmagnesium hexanoate, phenylmagnesium hexanoate, benzylmagnesium hexanoate), hydrocarbylmagnesium alkoxide (e.g. methylmagnesium ethoxide, ethylmagnesium ethoxide, butylmagnesium ethoxide, hexylmagnesium ethoxide, phenylmagnesium ethoxide, benzylmagnesium ethoxide), and hydrocarbylmagnesium aryloxide (e.g., methylmagnesium phenoxide, ethylmagnesium phenoxide, butylmagnesium phenoxide, hexylmagnesium phenoxide, phenylmagnesium phenoxide, and benzylmagnesium phenoxide).

The catalyst composition also or alternatively can contain a non-coordinating anion or a non-coordinating anion precursor. Exemplary non-coordinating anions include tetravalent B anions such as tetraarylborate anions, particularly fluorinated tetraarylborate anions. Specific examples of non-coordinating anions include tetraphenylborate, tetrakis(monofluorophenyl)borate, tetrakis(difluorophenyl)borate, tetrakis(trifluororphenyl)borate, tetrakis(tetrafluorophenyl)borate, tetrakis(pentafluorophenyl)borate, tetrakis(tetrafluoromethylphenyl)borate, tetra(tolyl)borate, tetra(xylyl)borate, (triphenyl, pentafluorophenyl)borate, [tris(pentafluorophenyl), phenyl]borate, tridecahydride-7,8-dicarbaundecaborate and the like. Tetrakis(pentafluorophenyl)borate is among the preferred non-coordinating anions.

Compounds containing a non-coordinating anion also contain a countercation such as a carbonium (e.g., trisubstituted carbonium cation such as triphenylcarbonium cation, tri(substituted phenyl)carbonium cation (e.g., tri(m-ethylphenyl)carbonium cation), oxonium, ammonium (e.g., trialkyl ammonium cations, N,N-dialkyl anilinium cations, dialkyl ammonium cations, etc.), phosphonium (e.g., triaryl phosphonium cations such as triphenyl phosphonium cation, tri(methylphenyl)phosphonium cation, tri(dimethylphenyl)-phosphonium cation, etc.), cycloheptatrieneyl, or ferrocenium cation (or similar). Among these, N,N-dialkyl anilinium or carbonium cations are preferred, with the former being particularly preferred.

Examples of compounds containing a non-coordinating anion and a counter cation include triphenylcarbonium tetrakis(pentafluorophenyl)borate, N,N-dimethylanilinium tetrakis(pentafluorophenyl)borate, triphenylcarbonium tetrakis[3,5-bis(trifluoromethyl)-phenyl]borate, and N,N-dimethylanilinium tetrakis[3,5-bis(trifluoromethyl)phenyl]borate.

Exemplary non-coordinating anion precursors include boron compounds that include strong electron-withdrawing groups. Specific examples include triarylboron compounds where each aryl group is strongly electron withdrawing, e.g., pentafluorophenyl or 3,5-bis(trifluoromethyl)phenyl.

Catalyst compositions of the type just described have very high catalytic activity for polymerizing polyenes such as conjugated dienes (and optionally olefins, particularly α-olefins) into stereospecific polymers over a wide range of concentrations and ratios, although polymers having the most desirable properties typically are obtained from systems that employ a relatively narrow range of concentrations and ratios of ingredients. Further, the catalyst ingredients are believed to interact to form an active catalyst species, so the optimum concentration for each ingredient can depend on the concentrations of the other ingredients. The following molar ratios are considered to be relatively exemplary for a variety of different systems based on the foregoing ingredients:

alkylating agent to lanthanide complex (alkylating agent/ Ln): from ~1:1 to ~1000:1, commonly from ~2:1 to ~500:1, typically from ~5:1 to ~200:1;

aluminoxane to lanthanide complex, specifically equivalents of aluminum atoms in the aluminoxane to equivalents of lanthanide atoms in the lanthanide complex (Al/Ln): from ~5:1 to ~1000:1, commonly from ~10:1 to ~700:1, typically from ~20:1 to ~500:1;

organoaluminum compound to lanthanide complex (oAl/ Ln): from ~1:1 to ~200:1, commonly from ~2:1 to ~150:1, typically from ~5:1 to ~100:1; and non-coordinating anion or precursor to lanthanide complex (An/Ln): from ~1:2 to ~20:1, commonly from ~3:4 to ~10:1, typically from ~1:1 to ~6:1.

The molecular weight of polymers produced with a lanthanide-based catalyst composition can be controlled by adjusting the amount of catalyst used and/or the amounts of co-catalyst concentrations within the catalyst system; polymers having a wide range of molecular weights can be produced in this manner. In general, increasing the catalyst and co-catalyst concentrations reduces the molecular weight of resulting polymers, although very low molecular weight polymers (e.g., liquid polydienes) require extremely high catalyst concentrations. Typically, this necessitates removal of catalyst residues from the polymer to avoid adverse effects such as retardation of the sulfur cure rate.

A lanthanide-based catalyst composition can be formed using any of the following methods:

(1) In situ. The catalyst ingredients are added to a solution containing monomer and solvent (or simply bulk monomer). The addition can occur in a stepwise or simultaneous manner. In the case of the latter, the alkylating agent preferably is added first followed by the lanthanide complex.

(2) Pre-mixed. The ingredients can be mixed outside the polymerization system, generally at a temperature of from about −20° to ~80° C., before being introduced to the monomer(s).

(3) Pre-formed in the presence of monomer(s). The catalyst ingredients are mixed in the presence of a small amount of monomer(s) at a temperature of from about −20° to ~80° C. The amount of conjugated diene monomer can range from ~1 to ~500 moles, commonly from ~5 to ~250 moles, typically from ~10 to ~100 moles, per mole of the lanthanide complex. The resulting catalyst composition is added to the remainder of the monomer(s) to be polymerized.

(4) Two-stage procedure.
  (a) The alkylating agent is combined with the lanthanide complex in the absence of monomer or in the presence of a small amount of monomer(s) at a temperature of from about −20° to ~80° C.
  (b) The foregoing mixture and the remaining components are charged in either a stepwise or simultaneous manner to the remainder of the monomer(s) to be polymerized.

When a solution of one or more of the catalyst ingredients is prepared outside the polymerization system in the foregoing methods, an organic solvent or carrier is preferably employed; useful organic solvents include those mentioned previously. In other embodiments, one or more monomers can be used as a carrier or the catalyst ingredients can be employed neat, i.e., free of any solvent of other carrier.

In one or more embodiments, some or all of the catalyst composition can be supported on an inert carrier. The support can be a porous solid such as talc, a sheet silicate, an inorganic oxide or a finely divided polymer powder. Suitable inorganic oxides are oxides of elements from any of Groups 2-5 and 13-16. Examples of preferred supports include $SiO_2$, aluminum oxide, and also mixed oxides of the elements Ca, Al, Si, Mg or Ti and also corresponding oxide mixtures, Mg halides, styrene/divinylbenzene copolymers, polyethylene or polypropylene.

The production of polymers such as cis-1,4-polydiene (or interpolymers that include cis-1,4-diene mer) is accomplished by polymerizing conjugated diene monomer(s) in the presence of a catalytically effective amount of a catalyst composition. The total catalyst concentration to be employed in the polymerization mass depends on the interplay of various factors such as the purity of the ingredients, the polymerization temperature, the polymerization rate and conversion desired, the molecular weight desired, and many other factors; accordingly, a specific total catalyst concentration cannot be definitively set forth except to say that catalytically effective amounts of the respective catalyst ingredients should be used. The amount of the lanthanide complex used generally ranges from ~0.01 to ~2 mmol, commonly from ~0.02 to ~1 mmol, typically from ~0.05 to ~0.5 mmol per 100 g monomer. All other ingredients generally can be added in amounts based on the amount of lanthanide complex; see the various ratios set forth above.

Where an olefin interpolymer is desired, the molar ratio of polyene (e.g., conjugated diene) to olefin introduced into the reaction vessel can vary over a wide range. For example, the molar ratio of polyene (e.g., conjugated diene) to olefin can range from ~100:1 to 1:100, commonly from ~20:1 to 1:20, and typically from ~5:1 to 1:5.

Polymerization preferably is carried out in one or more organic solvents of the type(s) set forth above, i.e., as a solution polymerization (where both the monomer(s) and the polymers formed are soluble in the solvent) or precipitation polymerization (where the monomer is in a condensed phase but the polymer products are insoluble). The catalyst ingredients preferably are solubilized or suspended in the organic liquid, and additional solvent (beyond that used in preparing the catalyst composition) usually is added to the polymerization system; the additional solvent(s) may be the same as or different from the solvent(s) used in preparing the catalyst system. In one or more embodiments, the solvent content of the polymerization mixture may be more than 20%, more than 50%, or even more than 80% (by wt.) of the total weight of the polymerization mixture. The concentration of monomer present at the beginning of the polymerization generally ranges from ~3 to ~80%, commonly from ~5 to ~50%, and typically from ~10% to ~30% (by wt.).

In certain embodiments, a bulk polymerization system that includes no more than a minimal amount of solvent can be used, i.e., a bulk polymerization process where one or more of the monomers act(s) as the solvent; examples of potentially useful bulk polymerization processes are disclosed in U.S. Patent Appl. Pub. No. 2005/0197474 A1. In a bulk polymerization, the solvent content of the polymerization mixture may be less than ~20%, less than ~10%, or even less than ~5% (by wt.) of the total weight of the polymerization mixture. The polymerization mixture even can be substantially devoid of solvent, i.e., contain less than that amount of solvent which otherwise would have an appreciable impact on the polymerization process.

The polymerization can be conducted in any of a variety of reaction vessels. For example, solution polymerizations can be conducted in a conventional stirred-tank reactor. Bulk polymerizations also can be conducted in a stirred-tank reaction if the monomer conversion is less than ~60%. Where monomer conversion is higher than ~60%, which typically results in a highly viscous polymer cement (i.e., reaction mixture), bulk polymerization can be conducted in an elongated reactor in which the viscous cement is driven by, for example, piston or self-cleaning single- or double-screw agitator.

All components used in or during the polymerization can be combined in a single vessel (e.g., a stirred-tank reactor), and the entirety of the polymerization process can be conducted in that vessel. Alternatively, two or more of the ingredients can be combined outside the polymerization vessel and transferred to another vessel where polymerization of the monomer(s), or at least a major portion thereof, can be conducted.

The polymerization can be carried out as a batch, continuous, or semi-continuous process. The conditions under which the polymerization proceeds can be controlled to maintain the temperature of the polymerization mixture in a range of from −10° to ~200° C., commonly from ~0° to ~150° C., and typically from ~20° to ~100° C. Heat generated by the polymerization can be removed by external cooling by a thermally controlled reactor jacket and/or internal cooling (by evaporation and condensation of the monomer through use of a reflux condenser connected to the reactor). Also, conditions may be controlled to conduct the polymerization under a pressure of from ~0.01 to ~5 MPa, commonly from ~0.05 to ~2 MPa, typically from ~0.1 to ~1 MPa; the pressure at which the polymerization is carried out can be such that the majority of monomers are in the liquid phase. In these or other embodiments, the polymerization mixture may be maintained under anaerobic conditions, typically provided by an inert protective gas such as $N_2$, Ar or He.

Regardless of whether a batch, continuous, or semi-continuous process is employed, the polymerization preferably is conducted with moderate to vigorous agitation.

The described polymerization process advantageously results in polymer chains that possess reactive (pseudo-living) terminals, which can be further reacted with one or more functionalizing agents so as to provide a polymer with a terminal functionality. These types polymers can be referred to as functionalized and are distinct from a propagating chain that has not been similarly reacted. In one or more embodiments, reaction between the functionalizing agent and the reactive polymer can proceed via an addition or substitution reaction.

The terminal functionality can be reactive or interactive with other polymer chains (propagating and/or non-propagating) or with other materials in a rubber compound such as particulate reinforcing fillers (e.g. carbon black). As described above, enhanced interactivity between a polymer and particulate fillers in rubber compounds improves the mechanical and dynamic properties of resulting vulcanizates. For example, certain functionalizing agents can impart a terminal functionality that includes a heteroatom to the polymer chain; such functionalized polymer can be used in rubber compounds from which vulcanizates can be provided, and that vulcanizates can possess high temperature (e.g., 50° C.) hysteresis losses that are less than those possessed by vulcanizates prepared from similar rubber compounds that do not include such functionalized polymers. Reductions in high temperature hysteresis loss can be at least 5%, sometimes at least 10%, and occasionally at least 15%.

The functionalizing agent(s) can be introduced after a desired monomer conversion is achieved but prior to introduction of a quenching agent (a compound with a protic H atom) or after the polymerization mixture has been partially quenched. The functionalizing agent can be added to the polymerization mixture after a monomer conversion of at least 5%, at least 10%, at least 20%, at least 50%, or at least 80%; in these or other embodiments, the functionalizing agent can be added to the polymerization mixture prior to a monomer conversion of 90%, prior to 70%, prior to 50%, prior to 20%, or prior to 15%. In certain embodiments, the functionalizing agent is added after complete, or substantially complete, monomer conversion. In particular embodiments, a functionalizing agent may be introduced to the polymerization mixture immediately prior to, together with, or after the introduction of a Lewis base as disclosed in U.S. Patent Publ. No. 2009/0043046 A1.

Useful functionalizing agents include compounds that simply provide a functional group at the end of a polymer chain without joining two or more polymer chains together, as well as compounds that can couple or join two or more polymer chains together via a functional linkage to form a single macromolecule. The ordinarily skilled artisan is familiar with numerous examples of terminal functionalities that can be provided through this type of post-polymerization functionalization with terminating reagents, coupling agents and/or linking agents. For additional details, the interested reader is directed to any of U.S. Pat. Nos. 4,015,061, 4,616,069, 4,906,706, 4,935,471, 4,990,573, 5,064,910, 5,153,159, 5,149,457, 5,196,138, 5,329,005, 5,496,940, 5,502,131, 5,567,815, 5,610,227, 5,663,398, 5,567,784, 5,786,441, 5,844,050, 6,812,295, 6,838,526, 6,992,147, 7,153,919, 7,294,680, 7,642,322, 7,671,136, 7,671,138, 7,732,534, 7,750,087, 7,816,483, 7,879,952, 8,063,153, 8,088,868, etc., as well as references cited in these patents and later publications citing these patents; see also U.S. Patent Publ. Nos. 2007/0078232, 2008/0027171, and the like. Specific exemplary functionalizing compounds include metal halides (e.g., $SnCl_4$), $R^8{}_3SnCl$, $R^8{}_2SnCl_2$, $R^8SnCl_3$, metalloid halides (e.g., $SiCl_4$), carbodiimides, ketones, aldehydes, esters, quinones, N-cyclic amides, N,N'-disubstituted cyclic ureas, cyclic amides, cyclic ureas, Schiff bases, iso(thio)cyanates, metal ester-carboxylate complexes (e.g., dioxtyltin bis(octylmaleate), 4,4'-bis(diethylamino)benzophenone, alkyl thiothiazolines, alkoxysilanes (e.g., $Si(OR^8)_4$, $R^8Si(OR^8)_3$, $R^8{}_2Si(OR^8)_2$, etc.), cyclic siloxanes, alkoxystannates, and mixtures thereof. (In the foregoing, each $R^8$ independently is a $C_1$-$C_{20}$ alkyl group, $C_3$-$C_{20}$ cycloalkyl group, $C_6$-$C_{20}$ aryl group, or $C_7$-$C_{20}$ aralkyl group.) Specific examples of preferred functionalizing compounds include $SnCl_4$, tributyl tin chloride, dibutyl tin dichloride, and 1,3-dimethyl-2-imidazolidinone (DMI).

The amount of functionalizing agent added to the polymerization mixture can depend on various factors including the amount of catalyst used, the type of functionalizing agent, the desired level of functionality, etc. In one or more embodiments, the amount of functionalizing agent may be in a range of from 1 to ~200 moles, commonly from ~5 to ~150 moles, and typically from ~10 to ~100 moles per mole of lanthanide complex.

Because reactive polymer chains can slowly self-terminate at high temperatures, the functionalizing agent can be added to the polymerization mixture once a peak polymerization temperature is observed or, at least in some embodiments, within ~25 to ~35 minutes thereafter. Reaction of these types of compounds with a terminally active polymer can be performed relatively quickly (a few minutes to a few hours) at moderate temperatures (e.g., 0° to 75° C.).

The functionalizing agent can be introduced to the polymerization mixture at a location (e.g., within a vessel) where the polymerization, or at least a portion thereof, has been conducted or at a location distinct therefrom. For example, the functionalizing agent can be introduced to the polymerization mixture in downstream vessels including downstream reactors or tanks, in-line reactors or mixers, extruders, or devolatilizers.

Although not mandatory, if desired, quenching can be performed to inactivate any residual reactive copolymer chains and the catalyst composition. Quenching can be conducted by stirring the polymer and an active hydrogen-containing compound, such as an alcohol or acid, for up to ~120 minutes at temperatures of from ~25° to ~150° C. In some embodiments, the quenching agent can include a polyhydroxy compound as disclosed in U.S. Pat. No. 7,879,958. An antioxidant such as 2,6-di-t-butyl-4-methylphenol (BHT) may be added along with, before, or after the addition of the quenching agent; the amount of antioxidant employed can be from ~0.2 to 1% (by wt.) of the polymer product. The quenching agent and the antioxidant can be added neat or, if necessary, dissolved in a hydrocarbon solvent or liquid monomer prior to being added to the polymerization mixture.

Once polymerization, functionalization (if any) and quenching (if any) are complete, the various constituents of the polymerization mixture can be recovered. Unreacted monomers can be recovered from the polymerization mixture by, for example, distillation or use of a devolatilizer. Recovered monomers can be purified, stored, and/or recycled back to the polymerization process.

The polymer product can be recovered from the polymerization mixture using known techniques. For example, the polymerization mixture can be passed through a heated screw apparatus, such as a desolventizing extruder, in which volatile substances (e.g., low boiling solvents and unreacted monomers) are removed by evaporation at appropriate temperatures (e.g., ~100° to ~170° C.) and under atmospheric or sub-atmospheric pressure. Another option involves steam desolvation followed by drying the resulting polymer crumbs in a hot air tunnel. Yet another option involves recovering the polymer directly by drying the polymerization mixture on a drum dryer. Any of the foregoing can be combined with coagulation with water, alcohol or steam; if coagulation is performed, oven drying may be desirable.

Recovered polymer can be grafted with other monomers and/or blended with other polymers (e.g., polyolefins) and additives to form resin compositions useful for various applications. The polymer, regardless of whether further reacted, is particularly suitable for use in the manufacture of various tire components including, but not limited to, tire treads, sidewalls, subtreads, and bead fillers. It also can be used as a compatibilizer for elastomeric blends and/or used in the manufacture of hoses, belts, shoe soles, window seals, other seals, vibration damping rubber, and other industrial or consumer products.

When the resulting polymer is utilized in a tread stock compound, it can be used alone or blended with any conventionally employed tread stock rubber including natural rubber and/or non-functionalized synthetic rubbers such as, e.g., one or more of homo- and interpolymers that include just polyene-derived mer units (e.g., poly(butadiene), poly(isoprene), and copolymers incorporating butadiene, isoprene, and the like), SBR, butyl rubber, neoprene, EPR, EPDM, acrylonitrile/butadiene rubber (NBR), silicone rubber, fluoroelastomers, ethylene/acrylic rubber, EVA, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from ~5 to ~99% of the total rubber, with the conventional rubber(s) making up the balance of the total rubber. The minimum amount depends to a significant extent on the degree of hysteresis reduction desired.

Amorphous silica ($SiO_2$) can be utilized as a filler. Silicas are generally classified as wet-process, hydrated silicas because they are produced by a chemical reaction in water, from which they are precipitated as ultrafine, spherical particles. These primary particles strongly associate into aggregates, which in turn combine less strongly into agglomerates. "Highly dispersible silica" is any silica having a very substantial ability to de-agglomerate and to disperse in an elastomeric matrix, which can be observed by thin section microscopy.

Surface area gives a reliable measure of the reinforcing character of different silicas; the Brunauer, Emmet and Teller ("BET") method (described in *J. Am. Chem. Soc., vol. 60*, p. 309 et seq.) is a recognized method for determining surface area. BET surface area of silicas generally is less than 450 $m^2$/g, and useful ranges of surface include from ~32 to ~400 $m^2$/g, ~100 to ~250 $m^2$/g, and ~150 to ~220 $m^2$/g.

The pH of the silica filler is generally from ~5 to ~7 or slightly over, preferably from ~5.5 to ~6.8.

Some commercially available silicas which may be used include Hi-Sil™ 215, Hi-Sil™ 233, and Hi-Sil™ 190 (PPG Industries, Inc.; Pittsburgh, Pa.). Other suppliers of commercially available silica include Grace Davison (Baltimore, Md.), Degussa Corp. (Parsippany, N.J.), Rhodia Silica Systems (Cranbury, N.J.), and J.M. Huber Corp. (Edison, N.J.).

Silica can be employed in the amount of ~1 to ~100 phr, preferably in an amount from ~5 to ~80 phr. The useful upper range is limited by the high viscosity that such fillers can impart.

Other useful fillers include all forms of carbon black including, but not limited to, furnace black, channel blacks and lamp blacks. More specifically, examples of the carbon blacks include super abrasion furnace blacks, high abrasion furnace blacks, fast extrusion furnace blacks, fine furnace blacks, intermediate super abrasion furnace blacks, semi-reinforcing furnace blacks, medium processing channel blacks, hard processing channel blacks, conducting channel blacks, and acetylene blacks; mixtures of two or more of these can be used. Carbon blacks having a surface area (EMSA) of at least 20 $m^2$/g, preferably at least ~35 $m^2$/g, are preferred; surface area values can be determined by ASTM D-1765 using the CTAB technique. The carbon blacks may be in pelletized form or an unpelletized flocculent mass, although unpelletized carbon black can be preferred for use in certain mixers.

The amount of carbon black can be up to ~50 phr, with ~5 to ~40 phr being typical. When carbon black is used with silica, the amount of silica can be decreased to as low as ~1 phr; as the amount of silica decreases, lesser amounts of the processing aids, plus silane if any, can be employed.

Elastomeric compounds typically are filled to a volume fraction, which is the total volume of filler(s) added divided by the total volume of the elastomeric stock, of ~25%; accordingly, typical (combined) amounts of reinforcing fillers, i.e., silica and carbon black, is ~30 to 100 phr.

When silica is employed as a reinforcing filler, addition of a coupling agent such as a silane is customary so as to ensure good mixing in, and interaction with, the elastomer(s). Generally, the amount of silane that is added ranges between ~4 and 20%, based on the weight of silica filler present in the elastomeric compound.

Coupling agents can have a general formula of A-T-G, in which A represents a functional group capable of bonding physically and/or chemically with a group on the surface of the silica filler (e.g., surface silanol groups); T represents a hydrocarbon group linkage; and G represents a functional group capable of bonding with the elastomer (e.g., via a sulfur-containing linkage). Such coupling agents include organosilanes, in particular polysulfurized alkoxysilanes (see, e.g., U.S. Pat. Nos. 3,873,489, 3,978,103, 3,997,581, 4,002,594, 5,580,919, 5,583,245, 5,663,396, 5,684,171, 5,684,172, 5,696,197, etc.) or polyorganosiloxanes bearing the G and A functionalities mentioned above. An exemplary coupling agent is bis[3-(triethoxysilyl)propyl]tetrasulfide.

Addition of a processing aid can be used to reduce the amount of silane employed. See, e.g., U.S. Pat. No. 6,525,118 for a description of fatty acid esters of sugars used as processing aids. Additional fillers useful as processing aids include, but are not limited to, mineral fillers, such as clay (hydrous aluminum silicate), talc (hydrous magnesium silicate), and mica as well as non-mineral fillers such as urea and sodium sulfate. Preferred micas contain principally alumina, silica and potash, although other variants also can be useful. The additional fillers can be utilized in an amount of up to ~40 phr, typically up to ~20 phr.

Other conventional rubber additives also can be added. These include, for example, process oils, plasticizers, anti-degradants such as antioxidants and antiozonants, curing agents and the like.

All of the ingredients can be mixed using standard equipment such as, e.g., Banbury or Brabender mixers. Typically, mixing occurs in two or more stages. During the first stage (often referred to as the masterbatch stage), mixing typically is begun at temperatures of ~120° to ~130° C. and increases until a so-called drop temperature, typically ~165° C., is reached.

Where a formulation includes silica, a separate re-mill stage often is employed for separate addition of the silane component(s). This stage often is performed at temperatures similar to, although often slightly lower than, those employed in the masterbatch stage, i.e., ramping from ~90° C. to a drop temperature of ~150° C.

Reinforced rubber compounds conventionally are cured with ~0.2 to ~5 phr of one or more known vulcanizing agents such as, for example, sulfur or peroxide-based curing systems. For a general disclosure of suitable vulcanizing agents, the interested reader is directed to an overview such as that provided in Kirk-Othmer, *Encyclopedia of Chem. Tech.*, 3d ed., (Wiley Interscience, New York, 1982), vol. 20, pp. 365-468. Vulcanizing agents, accelerators, etc., are added at a final mixing stage. To ensure that onset of vulcanization does not occur prematurely, this mixing step often is done at lower temperatures, e.g., starting at ~60° to ~65° C. and not going higher than ~105° to ~110° C.

The following non-limiting, illustrative examples provide the reader with detailed conditions and materials that can be useful in the practice of the present invention.

EXAMPLES

Example 1

Nd Complex

A mixture of 59 mg NaH (2.44 mmol) and 600 mg N,N'-bis(3,5-di-tert-butyl-salicylidene)ethylenediamine (1.22 mmol) in 12 mL THF was refluxed for ~40 minutes. To the resulting yellow solution was added 481 mg NdCl$_3$(THF)$_2$ (1.22 mmol), and this mixture was refluxed for ~6 hours.

The reaction mixture was filtered through diatomaceous earth, with the filter cake being washed with THF. The combined filtrates were evaporated under vacuum to give 880 mg of a lemon-yellow solid having the following structure:

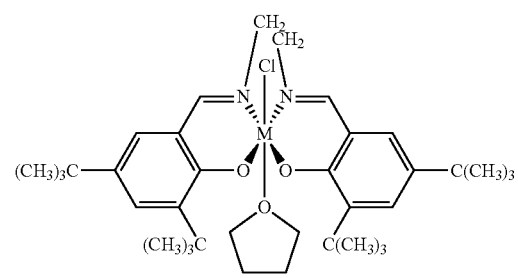

Examples 2-6

Polybutadienes

To a N$_2$-purged dry bottle was added 0.96 mL of 1,3-butadiene in hexane (21.2%), 8.4 mL toluene, 2.9 mL MAO (4.32 M in toluene), and 92 mg of the Nd complex from Example 1, followed by 2.6 mL diisobutylaluminum hydride (DIBAH, 1.0 M in hexane). This catalyst composition (0.0083 M Nd) was aged at room temperature for ~20 minutes before use below.

To five N$_2$-purged dry bottles with self-sealing rubber lines and perforated metal caps were added 97 g hexane and 236 g 1,3-butadiene solution (21.2% in hexane). The following amounts of the catalyst solution from the preceding paragraph were added to the bottles (with the parenthetical number being the resulting amount of Nd complex):

Ex. 2—1.8 mL (0.030 mmol)
Ex. 3—2.1 mL (0.035 mmol)
Ex. 4—2.4 mL (0.040 mmol)
Ex. 5—2.7 mL (0.045 mmol)
Ex. 6—3.0 mL (0.050 mmol)

Each bottle was tumbled in a 65° C. water bath for ~60 minutes. Each polymer cement was quenched with 3 mL isopropanol containing 12% (by wt.) BHT before being coagulated in 2 L isopropanol containing 0.5 g BHT. The resulting polymers were drum-dried.

The properties of these polymers are summarized in the following table, with the molecular weight data and microstructure data being determined by, respectively, GPC and FTIR. Mooney viscosity (ML$_{1+4}$) values were determined with an Alpha Technologies™ Mooney viscometer (large rotor) using a one-minute warm-up time and a four-minute running time.

TABLE 1

Properties of polymers from Examples 2-6

|  | 2 | 3 | 4 | 5 | 6 |
|---|---|---|---|---|---|
| polymer yield, % | 92.8 | 94.8 | 95.4 | 96.2 | 96.6 |
| ML$_{1+4}$ @ 100° C. | 47.4 | 37.6 | 30.8 | 25.0 | 20.5 |
| cis BD mer, mol % | 94.7 | 93.3 | 91.8 | 90.7 | 89.7 |
| trans BD mer, mol % | 4.8 | 6.1 | 7.6 | 8.7 | 9.7 |

TABLE 1-continued

Properties of polymers from Examples 2-6

|  | 2 | 3 | 4 | 5 | 6 |
|---|---|---|---|---|---|
| 1,2-vinyl BD mer, mol % | 0.6 | 0.6 | 0.6 | 0.6 | 0.6 |
| $M_n$ (kg/mol) | 140.1 | — | — | — | — |
| $M_w/M_n$ | 1.90 | — | — | — | — |

Example 7

Copolymer

To a $N_2$-purged dry bottle was added 0.77 mL of 1,3-butadiene in hexane (21.5%), 6.8 mL toluene, 2.3 mL MAO (4.32 M in toluene), and 75 mg of the Nd complex from Example 1, followed by 2.1 mL DIBAH (1.0 M in hexane). This catalyst composition (0.0083 M Nd) was aged at room temperature for ~20 minutes before use below.

To a dry 3.8 L reactor purged with ethylene was charged 816 g hexane and 1.12 kg 1,3-butadiene solution (21.5% in hexane); this reactor was pressurized to 0.2 MPa with ethylene. The catalyst composition from the preceding paragraph was charged into the reactor, the reactor was pressurized to 1.7 MPa with ethylene, and the reactor jacket temperature was set to 66° C. Polymerization was allowed to proceed for ~4 hours.

The polymer cement was cooled and coagulated with 10 L isopropanol containing 4 g BHT, with the resulting polymers being drum-dried.

The amount of polymer recovered was 47.7 g. As determined by $^1$H NMR, the polymer contained ~3.2 mole percent ethylene mer. The butadiene mer incorporated almost essentially completely in 1,4-form, i.e., the vinyl content was ~0.7 mole percent. The $M_n$ of the polymer was 195,000 Daltons, and the $M_w/M_n$ was ~2.42.

The foregoing examples have employed ethylene as an exemplary olefin and 1,3-butadiene as an exemplary polyene. These choices were made in view of a variety of factors including cost, availability and ability to handle. From the foregoing examples employing these materials, the ordinarily skilled artisan will be able to extend these examples to a variety of homo- and interpolymers.

That which is claimed is:

1. A catalyst composition comprising a catalyst activator and a lanthanide metal complex of the general formula

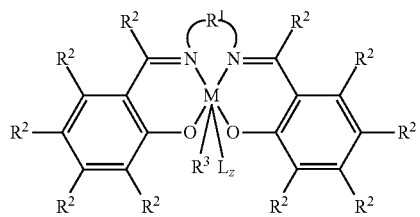

where
M represents a Nd or Gd atom;
L represents a neutral Lewis base;
z is an integer of from 0 to 2 inclusive, with the proviso that each L is the same when z is 2;
$R^1$ is a divalent atom or group that contains at least one C,O,S,N,P,Si,Se,Sn or B;
each $R^2$ independently is H, a halogen atom, substituted or unsubstituted hydrocarbyl group, the radical of a heterocyclic compound, or a heteroatom-containing group; and
$R^3$ is a halogen containing group, a group that contains an Al atom, or $R^2$, with the proviso that (1) two $R^2$ groups together with the atoms to which each is bonded can form a ring structure, (2) one $R^2$ group and $R^1$ $R^3$ together with the atoms to which each is bonded can form a ring structure, and/or (3) $R^1$ and $R^3$ together with the atoms to which each is bonded can form a ring structure.

2. The catalyst composition of claim 1 wherein L is tetrahydrofuran.

3. The catalyst composition of claim 1 wherein $R^3$ is a halogen atom.

4. The lanthanide metal complex of claim 1 wherein z is 1.

5. The catalyst composition of claim 1 wherein said catalyst activator comprises an alkylating agent.

6. The catalyst composition of claim 1 wherein said catalyst activator comprises a non-coordinating anion.

7. The catalyst composition of claim 1 wherein said catalyst activator comprises a non-coordinating anion precursor.

8. The catalyst composition of claim 1 wherein
said catalyst activator comprises (1) an alkylating agent that is an organoaluminum compound or an organomagnesium compound and (2) a non-coordinating anion or a non-coordinating anion precursor,
L represents tertahydrofuran , and
$R^3$ represents a halogen atom.

9. A process for providing a polymer, said process comprising contacting one or more ethylenically unsaturated hydrocarbon monomers with the catalyst composition of claim 1, thereby providing said polymer.

10. The process of claim 9 wherein said one or more ethylenically unsaturated hydrocarbon monomers comprises at least one type of polyene.

11. The process of claim 10 wherein said at least one type of polyene comprises one or more conjugated dienes.

12. The process of claim 10 wherein said one or more ethylenically unsaturated hydrocarbon monomers further comprises at least one type of α-olefin.

13. The process of claim 12 wherein said at least one type of α-olefin comprises ethylene.

14. The process of claim 13 wherein said contacting occurs in a solvent system that comprises a $C_5$-$C_{12}$ aliphatic alkane.

15. The process of claim 14 wherein said solvent system comprises hexane.

16. The process of claim 15 wherein said polymer comprises about 3 mole percent ethylene.

17. The process of claim 15 wherein said polymer comprises less than 1 mole percent of conjugated diene mer in a vinyl configuration.

18. The process of claim 9 further comprising reacting said polymer with a functionalizing agent so as to provide terminal functionality to said polymer.

* * * * *